United States Patent [19]
Fritzsche et al.

[11] Patent Number: 5,187,106
[45] Date of Patent: Feb. 16, 1993

[54] METHOD AND APPARATUS FOR HOMOGENEOUS FLUORESCENCE MEASUREMENTS

[75] Inventors: Robert W. Fritzsche, Bernardsville, N.J.; Kenneth J. Schlager, Elm Grove, Wis.

[73] Assignee: Orbit Medical Systems, Inc., Capistrano Beach, Calif.

[21] Appl. No.: 645,567

[22] Filed: Aug. 30, 1984

[51] Int. Cl.$^5$ .................. G01N 33/536; G01N 33/542
[52] U.S. Cl. .................... 436/501; 436/536; 436/537; 436/800
[58] Field of Search ............... 436/172, 537, 800, 501, 436/536

[56] References Cited

U.S. PATENT DOCUMENTS

| | | | |
|---|---|---|---|
| 4,006,360 | 2/1977 | Mueller | 250/461.2 |
| 4,058,732 | 11/1977 | Wieder | 250/461.1 |
| 4,352,751 | 10/1982 | Wieder et al. | 436/500 |

OTHER PUBLICATIONS

E. Soini et al *Clin. Chem.* 25, 353-361, 1979.
F. J. Knorr et al *Anal. Chem.*, 53, 272-276, 1981.
F. Komen et al, *Steroids,* 36, 421-427, 1980.

*Primary Examiner*—David A. Saunders

[57] ABSTRACT

A fluorescence decay time method and apparatus directly measuring the time decay function resulting from a plurality of fluorescing bodies, including background, and analytically determines the presence and concentration of the fluorescing bodies homogeneously and simultaneously is disclosed.

The fluorescently labelled reaction product of a target ligand, such as an antigen, with a binding molecule for the ligand, such as an antibody, exhibits a fluorescent decay time curve which bears a direct straight line relationship to the concentration of the target antigen, in that the value for fluorescent intensity at time zero for the decay time curve is a measure of said concentration.

The time zero intensity is proportional to the concentration of the target ligand in the unknown sample which can then be compared to the concentrations from a standard curve.

15 Claims, 6 Drawing Sheets

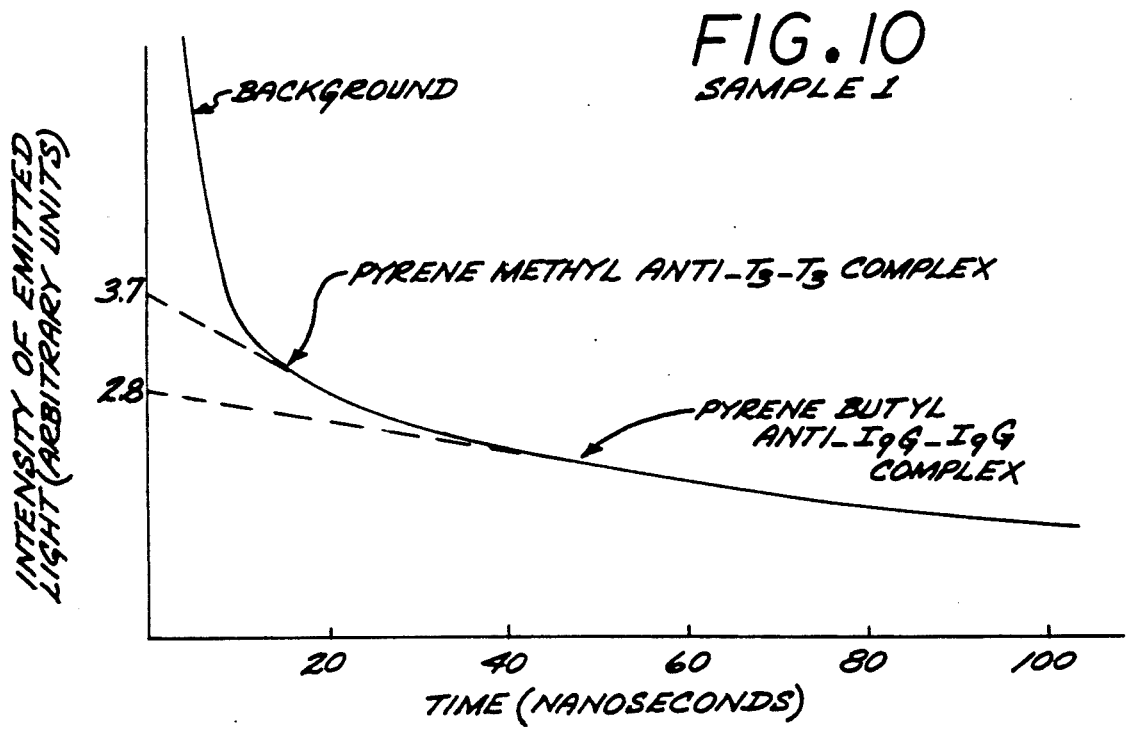
FIG. 10 SAMPLE 1
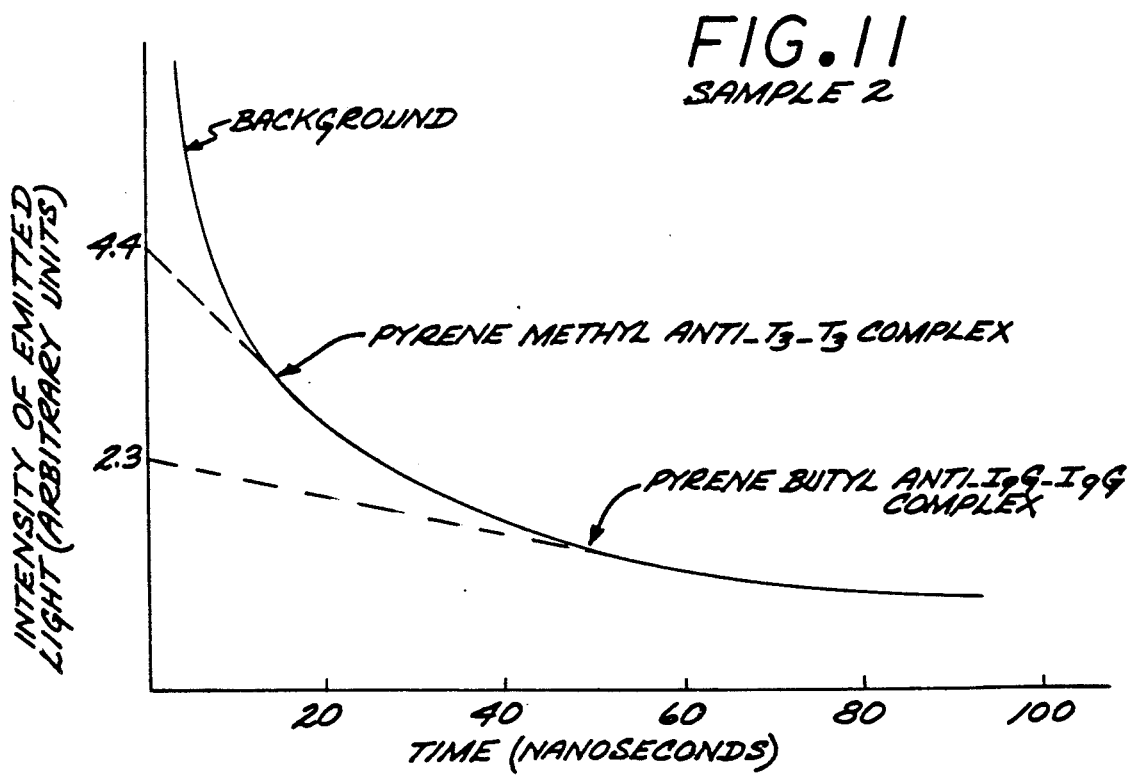
FIG. 11 SAMPLE 2

METHOD AND APPARATUS FOR HOMOGENEOUS FLUORESCENCE MEASUREMENTS

BACKGROUND OF THE INVENTION

1. The Field of Invention

This invention relates to an apparatus and method for conducting fluorometric measurements and more particularly to homogeneous fluorescent immunoassays. Finally, it relates to the determination of the presence and concentrations of a plurality of fluorescing bodies (and indirectly non-fluorescing bodies) simultaneously and homogeneously.

2. The Prior Art

Fluorescence technology has become widespread in the fields of clinical laboratory testing, research and medical diagnostic testing areas. It is widely regarded as a technique for making very sensitive and specific test determinations, competing effectively in many areas with radioimmunoassays and enzyme immunoassays.

Fluorescence is the physical phenomenon occurring when a molecule or atom is bombarded with light of given wavelengths; namely the conversion of that light to an emission of light of a different wavelength. In macroscopic terms, the conversion is instantaneous, but in real terms the finite time differences between the absorption of the light by the molecule and the time interval during which the emitted light is given off is a measure of the characteristics of the bodies being measured.

The process of fluorescence starts with the absorption of light photons by atoms or molecules. The frequency of light absorption varies with the atom or molecule involved.

Fluroescent molecules in any specific environment have two characteristic spectra. The first, the so-called excitation spectrum, is represented by a series of wavelengths of light which are absorbed by the molecule with differing efficiencies. That is, out of a possible number of existing wavelengths which may be absorbed by the molecule to cause fluorescence, usually one of these will be absorbed at a greater level. Most atoms or molecules that absorb light convert this light energy into heat, but a few emit light or "fluoresce" at a lower light frequency. Photon absorption occurs rapidly in about $10^{-15}$ seconds. If the light excitation is abruptly interrupted, as with a very short pulse of light, photon light emission, in the second spectrum will decay rapidly with a time constant that depends on the atom or molecule involved. The range of decay times is usually between $10^{-10}$ to $10^{-6}$ seconds (0.1 to 1000 nanoseconds). The intensity of the emission spectrum is directly proportional to the intensity of the exciting light.

It happens also that the intensity of the emitted light is also directly proportional to the concentration of the fluorescent molecules in the sample. It thus can be seen that a very sensitive technique for measuring the concentration of a fluorescent body can be evolved by controlling the intensity of the exciting light and other physical constants of the measuring system.

The analytical value of fluorescence decay time measurement arises from the fact that each atom or molecule has its own distinctive rate of decay. Each atom or molecule is excited at a different frequency and emits light only at a particular emission wavelength. Problems arise, however, when substances under test have overlapping emission wavelengths. In these instances, decay time measurement often becomes the only means of discrimination between differing fluorescing bodies.

An example of such overlapping emission wavelengths occurs in clinical tests of human blood serum. A variety of substances in blood serum fluoresce at the same wavelengths as the fluorochromes used in fluoroimmunoassay. Fortunately, these blood serum components have very short decay times (of the order of 1-10 nanoseconds), and using a decay time measurement, the substance of interest, such as a fluorochrome in fluoroimmunoassay, may be separately determined by these differences in decay times and by measuring the emission at wavelengths substantially different from the emission wavelengths of the background. This has not been an altogether satisfactory technique, however.

More recently the art has sought to take advantage of the decay characteristics of the emission spectra of a fluorescing body in an attempt to discriminate background fluorescence from the fluorescing body under study. For example, in U.S. Pat. No. 4,058,732 issued to Weider on Nov. 15, 1977, the inventor describes the excitation of target molecules (the substances to be measured) tagged with a fluorescent tag having a relatively long fluorescent decay lifetime compared to the decay lifetime of ambient or background substances. A fluorescent detection system is programmed to read the resulting fluorescence only after the fluorescence of the background has substantially decayed. Thus, the only fluorescence detected is that of the tagged substance, the ambient fluorescence having been allowed to disappear. The technique requires in addition that the excess fluorescent tag be separated from the tagged substance to be measured. More about this type of technique will be described below. The decay time measurements are taken over a short time interval in the nanosecond ($10^{-9}$ seconds) range usually 2-150 nanoseconds. Typically, ambient decay times are about 2-10 nanoseconds with specific tagged fluorescent material being in the range of 15 to 100 nanoseconds.

U.S. Pat. No. 4,006,360 to Mueller issued Feb. 1, 1977 also utilizes the longer decay lifetimes of bound fluorescing materials. This technique similarly utilizes a time-gating to discriminate between emissions from two populations of fluorescent dye molecules which exhibit different excited state lifetimes. In addition, the technique includes measuring the fluorescence over a predetermined time interval.

Similarly, "Biochemical Applications of a Synchronously Pumped Krypton Ion Dye Laser Flouorescence System," by Richardson et. al., Analytical Biochemistry 97, 17-23 (1979), describes other populations of fluorescent dye molecules which exhibit different excited state lifetimes depending on whether they are free, or attached to antibodies or antigen/antibody complexes.

U.S. Pat. No. 4,259,574 issued Mar. 31, 1981 to Carr & Froot relates basically to the determination of impurities or amalgams in semiconductor materials as measured by changes in the decay lifetime of the contaminated semiconductors versus a record of known fluorescent decay rates of the pure, unaltered molecular semiconductor.

There are a wide variety of prior art techniques which can be used to conduct immunoassays irrespective of the particular tag or label used. Typically, an immunoassay may involve, for example, competitive binding in which the antigen (drug, hormone, virus, or prokaryotic, eukaryotic or somatic cells, for example)

to be determined, and its corresponding antibody are combined with the identical antigen labelled appropriately. Both the labelled and nonlabelled antigens compete for antibody binding sites. The amount of labelled antigen which binds to the antibody is dependent upon, and therefore a measurement of, the concentration of nonlabelled antigen. The determination requires separation of the reacted labelled antigen from the unreacted labelled antigen. This is thus termed a heterogeneous assay.

In another method, the so-called sandwich method, the antibody is bound to a suitable solid support, such as the wall of a plastic test tube, small glass or plastic beads, or SEPHADEX particles (to facilitate later separation). This solid, antibody-coated material is then exposed to a solution of the unknown antigen, permitting antigen/antibody reaction to take place at the solid phase surface. The surface is washed and exposed to a solution of labelled antibody specific for the unknown antigen, permitting its binding with the exposed antigen. Excess unreacted labelled antibody is separated from the bound material, leaving the remaining fluorescence as a measurement of the target antigen in the biological sample.

There are several other formats for immunoassays some of which require separation of the unreacted tagged material from the reached tagged complexes.

BRIEF DESCRIPTION OF THE DRAWINGS

The invention and the prior art will be better understood by reference to the accompanying drawings wherein, FIG. 10 shows a decay time curve for Sample 1, FIG. 11 shows a decay time curve for Sample 2.

Figure 1:
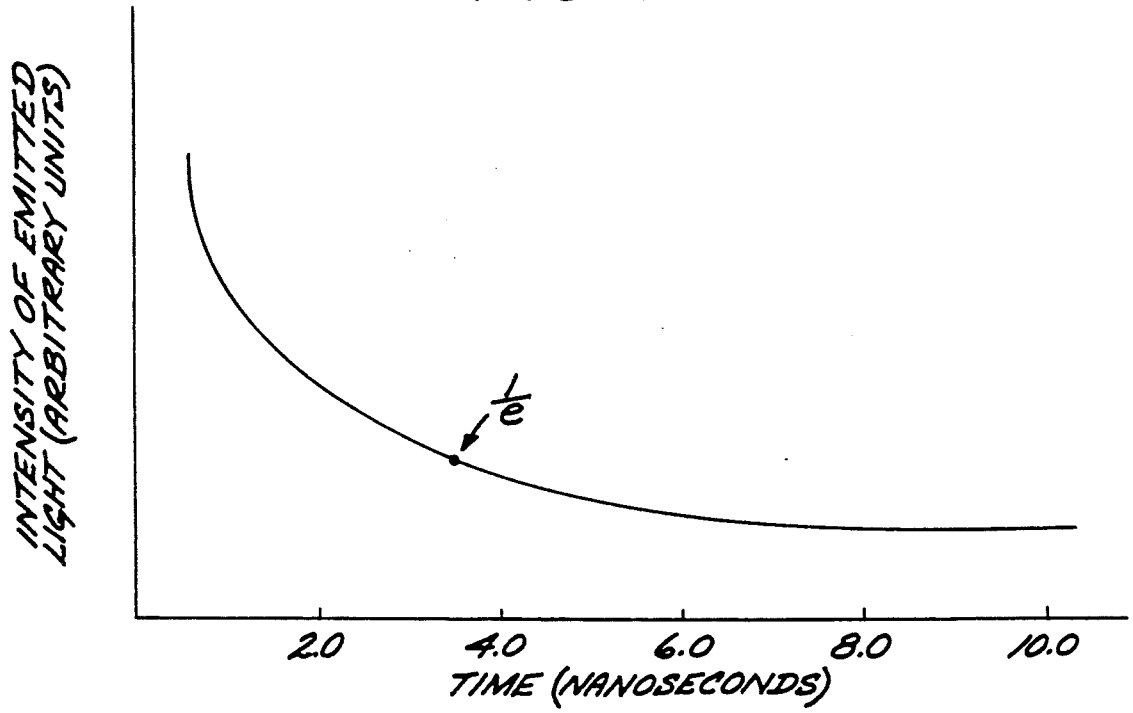
FIG. 1 is a typical fluorescence decay time curve.

In a typical fluorescent immunoassay using serum as the sample material for example, the contribution of the background fluorescence makes the detection of other fluorescing bodies, whose presence is critical to know, difficult or impossible to determine. If one were to excite, for the sake of simplicity, a liquid sample such as serum to cause it to emit fluorescence, a decay time curve of the type shown in FIG. 1 would be obtained. The vertical coordinate represents the log of a parameter which is proportional to fluorescent intensity such as voltage (e.g., the amount of voltage generated by the corresponding amount of emitted light as determined by a photo multiplier tube) and the horizontal coordinate, represents the time in nanoseconds. A total fluorescent lifetime of the order of 10 nanoseconds or so is typically observed. The decay time itself is generally that time required for the fluorescence to decay from its original peak intensity to 1/e times that original peak intensity, where e is the natural logarithm base.

If one were now to excite a serum sample in which the reagents for a fluorescent immunoassay were present including tagged antibody reacted with appropriate antigen in the sample, the fluorescent characteristics of the sample would be a composite.

The fluorescence decay curve obtained on such a mixture would be the net effect of all the decaying fluorescence of bodies in the mixture. If it were possible to obtain extremely high resolution of decay times versus fluorescent intensity one could obtain in theory, a separate exponential decay curve for each fluorescing body. In practice, however, since resolution of these curves is achieved at the nanosecond level, the resulting curve represents the sum of all fluorescing bodies obtained at the given nanosecond under study.

Figure 2:
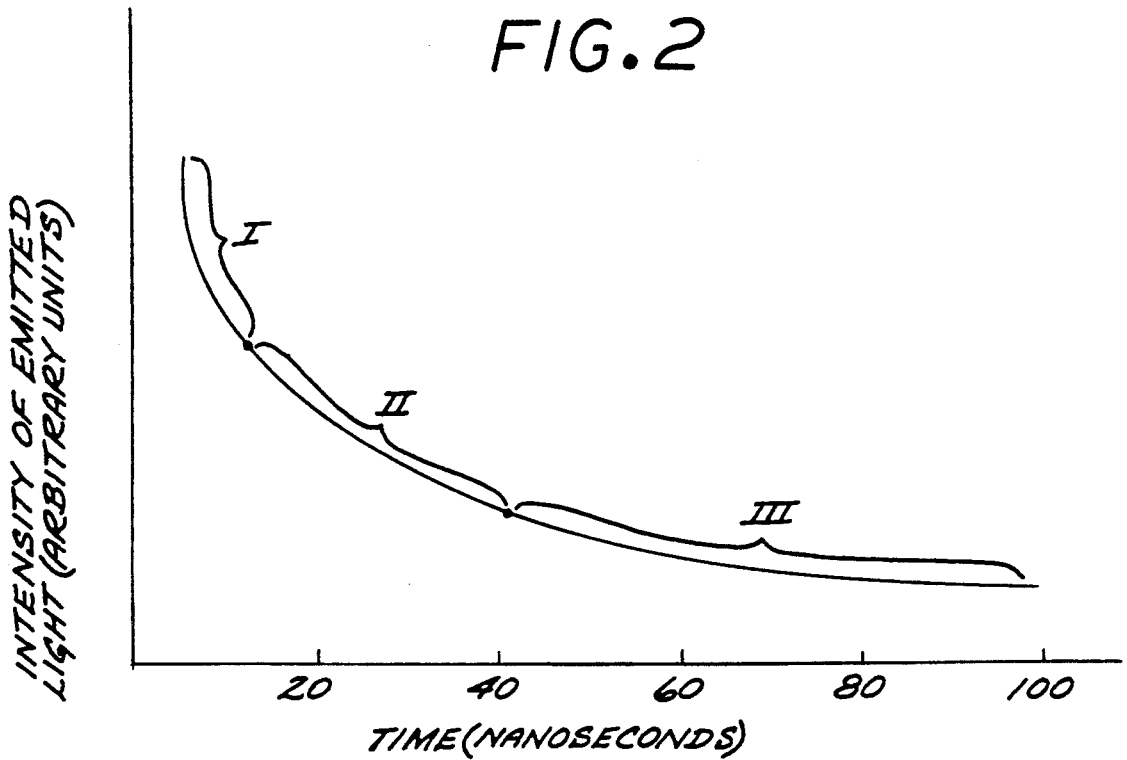
FIG. 2 shows a fluorescence decay time curve for two antigens (regions II and III), and background (region I)

FIG. 2 is typical of such a decay time curve where the target antigens, i.e., the antigens sought to be determined, are two in number. In such a case, the curve generally displays three distinct regions. Region I is background fluorescence, Region II is the composite fluorescence associated with a first target antigen and Region III is the composite fluorescence associated with a second target antigen. If there were more than two target antigens being detected the decay time curve would have correspondingly more Regions. It should be appreciated by those skilled in the art that the composite fluorescence displayed by the mixture is derived from the sample and components used to detect the antigen. Thus, for example, contributions to fluorescence will come from the unreacted labelled antibody as well as from the complex formed by the labelled antibody and the target antigen. As will be seen below, in accordance with the present invention, the components of the reaction all uniquely and reproducibly contribute to the fluorescence, given considerations of concentration, excitation energy and the like. This facilitates preparation of a standard curve as will be described more fully hereinafter.

SUMMARY OF THE INVENTION

The decay time method and apparatus of the present invention directly measures the time decay function resulting from a plurality of fluorescing bodies, including background, and analytically determines the presence and concentration of the pertinent fluorescing bodies of this decay function.

The invention is based on the discovery that the fluorescently labelled reaction product of a target ligand, such as an antigen, with a binding molecule for the ligand, such as an antibody, exhibits a fluorescent decay time curve which bears a direct straight line relationship to the concentration of the target antigen, in that the value for fluorescent intensity at time zero for the decay time curve is a measure of said concentration.

The intensity at time zero is obtained by extrapolation of that region of the curve relating to the target ligand, (II, or III in FIG. 2) to time zero as will be discussed hereinafter. The intercept intensity that is obtained is proportional to the concentration of the target ligand in the unknown sample which can then be compared to the concentrations from a standard curve. Although the preparation of standard curves are well within the skill of the art, details of preparations will be discussed below to facilitate practice of the invention.

Whether or not there is in fact an intensity at time zero for the particular antigen/antibody complex of interest is irrelevant. The invention simply uses the value that is obtained from the handling of the data as though there were a value at time zero. The best straight line for extrapolation can be fitted manually using conventional curve fitting techniques, or it can be obtained using known linear regression methods. The least squares procedure optimized by a reiterative simplex routine computer program is most preferred in the present invention. This technique is likewise within the skill of the art. See, for example, S. M. Deming and S. L. Morgan, Anal. Chem. 45 278A (1973) and F. S. Knorr and J. M. Harris, Anal. Chem. 53 272 (1981).

Once the extrapolated value for intensity at time zero is obtained, and especially when a plurality of target ligands such as is involved in the present invention, it becomes necessary to correlate the intensity associated with one particular Region of the curve (for example Region II of FIG. 2) with the appropriate and corresponding intensity obtained in preparation of the standard curve for the same antigen.

To facilitate this, one may prepare a separate standard curve for each ligand in which the concentrations are varied over the range expected to be encountered in practice and the fluorescing decay time curve (and decay time) established for that antigen-antibody labelled complex. That region of the composite decay time curve on the unknown which corresponds in terms of appropriate time of occurrence on the decay time curve obtained on the known sample is then taken as the Region to be extrapolated and correlated. The invention will now be explained more fully with reference to the accompanying figures and using an antigen as the target ligand for ease of reference.

In general, the procedure of the invention involves selecting samples having a known amount of the antigen which is ultimately to be detected in the unknowns. Several such samples are selected each having a different known level of antigen. These will serve as the samples from which a standard curve will be prepared. A sufficient number of levels is chosen to be statistically significant. They are termed herein as "Standards".

In practicing the invention, a first decay time curve is obtained on the antigen of interest by conducting a fluorescent immunoassay on one or more of the standards referred to above using the same reagents that will be used subsequently on the unknown. This need not necessarily be done on Standards where the concentration is known but it is preferred to do so. The purpose here is simply to establish the approximate decay time for the antigen/labelled-antibody complex and the decay time curve to serve as a reference point for later use in handling the results obtained on the unknowns. These are referred to herein as Reference Decay Time Curves. It is preferred, though not necessary, to determine the decay time.

In preparing the standard curve for use in the present invention, it is preferred to use samples which contain in known amounts a mixture of the antigens to be detected. This will save time and provide economies because of the minimization of the number of samples that are used.

The foregoing will be more fully understood in view of the following which will illustrate the process of the invention. Assume the ligands to be detected in a serum sample are antigens $Ag_1$ and $Ag_2$ and are present in the sample in unknown concentrations. Antibodies reactive to the antigens are selected as the binding molecules and are designated $Ab_1$ and $Ab_2$. Each of these antibodies is labelled with a fluorophore.

In the preferred embodiment of the invention a different fluorophore is attached to each antibody. Thus, fluorophore X is used for $Ab_1$, and fluorophore Y is used for $Ab_2$. Standard solutions containing known quantities of $Ag_1$ and $Ag_2$, usually three to five different levels are selected.

The test components are then as follows:

The sampel Contains Antigen $Ag_1$ and $Ag_2$ Labelled Antibodies: $Ab_1X$, $Ab_2Y$ Standards for Preparation of Standard Curve and for Reference Decay Time Curves:

1. $Ag_1 + Ag_2$ each at low abnormal Concentrations
2. $Ag_1 + Ag_2$ each at a low normal Concentration
3. $Ag_1 + Ag_2$ each at a normal Concentration
4. $Ag_1 + Ag_2$ each at high normal Concentrations
5. $Ag_1 + Ag_2$ each at high abnormal Concentrations

PREPARATION OF REFERENCE DECAY TIME CURVE

Two separate reactions are conducted, the object of which is to obtain the Reference Decay Time Curve for the target antigen so as to locate at least approximately its general position on the time-intensity curve. In that regard, any one of the above standards may be selected irrespective of the concentration of the antigen, since concentration affects only the intensity reading and not the time reading.

Figure 3:
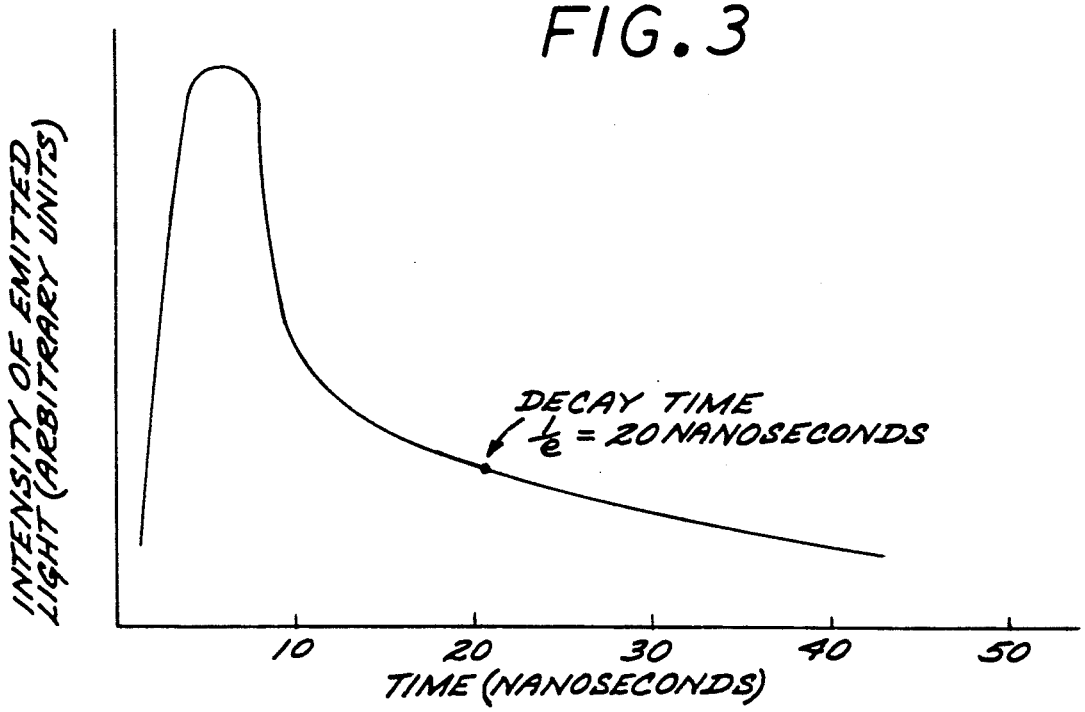
FIG. 3 shows a reference decay time curve for an antibody-antigen complex having a relatively short decay time.
Figure 4:
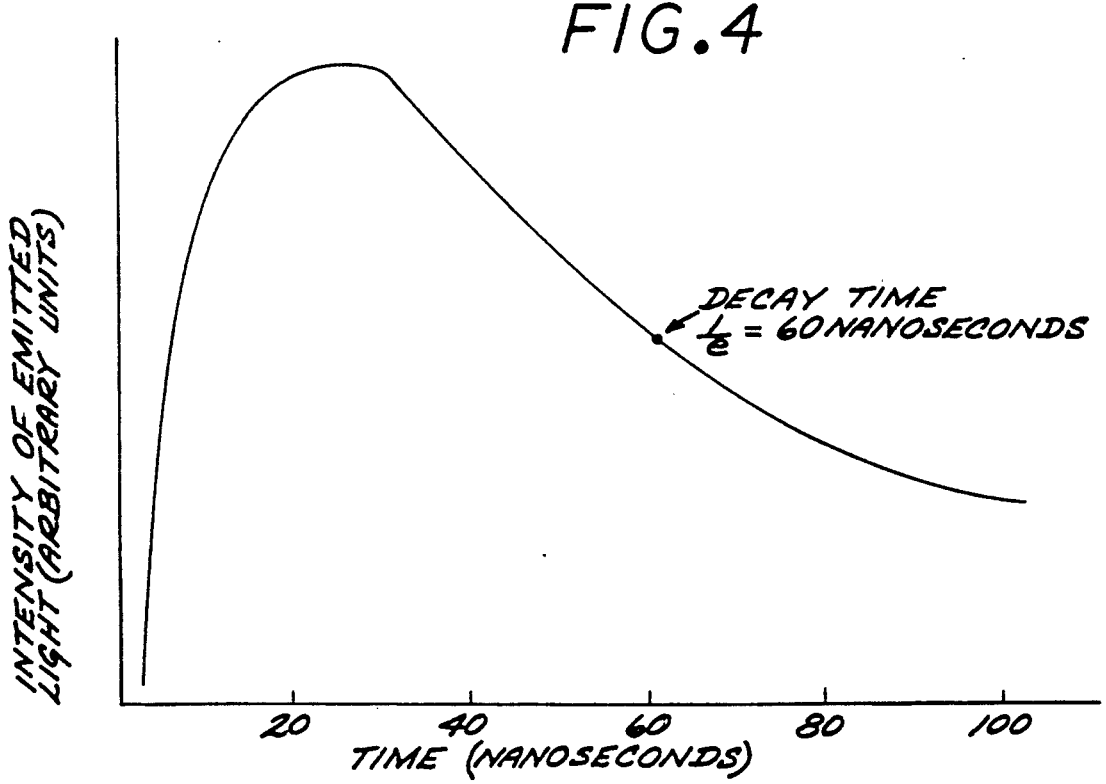
FIG. 4 shows a reference decay time curve for an antibody-antigen complex having a relatively long decay time.

Since there may be two or more target antigens, a Reference Decay Time Curve is prepared for each. Using $Ag_1$ as an example, an amount of $Ab_1 X$ is mixed with any of the above standards and using techniques known in the art, the reaction allowed to proceed. Thereafter a decay time curve is prepared using techniques known in the art. This procedure is repeated for all antigens of interest. FIGS. 3 and 4 are illustrations of the type of curves obtained, FIG. 3 being for a labelled antibody-antigen complex having a relative short decay curve ($Ag_1$ for example) and FIG. 4, being for a labelled antibody-antigen complex having a longer decay time curve, ($Ag_2$ for example). The curves so obtained are termed herein Reference Decay Time Curves. If desired, the decay time for each complex may be calculated and that figure used to locate appropriate Regions from the composite curve obtained on the immunoassay of the unknown.

PREPARATION OF STANDARD CURVE

A mixture of the labelled antibodies $Ab_1X$ and $Ab_2Y$ is added to the standards 1 through 5. The antibodies are preferably used in an amount known to be needed for the levels of antigen present in the control. Using techniques known in the art, the reaction is allowed to proceed. After the appropriate time the following represents the components of the mixture. $Ag_1 + Ag_2 + Ab_1X + Ab_2Y \rightleftharpoons Ag_1 \quad Ag_1X + Ag_2 \quad Ab_2Y + Ab_1X + Ab_2Y$ It can be assumed that in the reaction mixture obtained there will be all of the components shown. In most conventional heterogeneous immunoassays, at this point, the free labelled antibodies $Ab_1X$ and $Ab_2Y$ would have to be physically separated from the bound labelled antibodies before any reading of the desired reacted product could be undertaken. The present invention, however, does not require a separation step.

Figure 5:
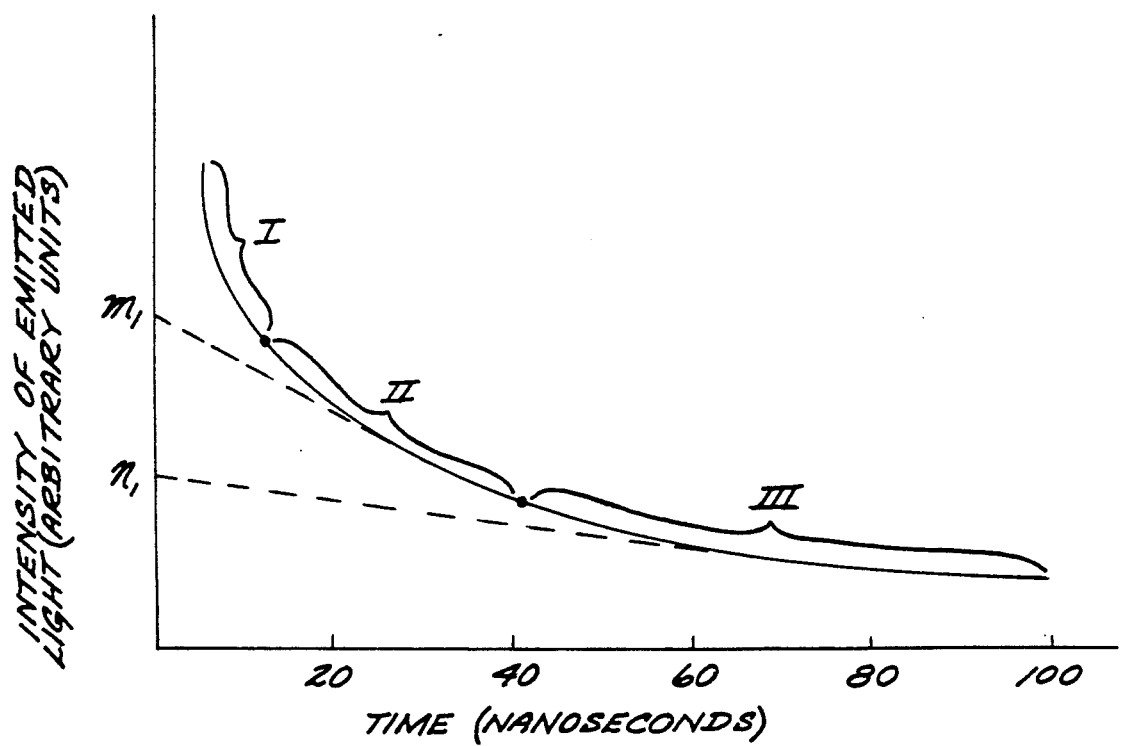
FIG. 5 shows a composite decay time curve for background corresponding to region I, a relatively short-lived antigen (region II), and a relatively long-lived antigen (region III) wherein extrapolations are made to zero time, yielding values m and n for antigens II and III respectively.

The fluorescent decay time curve for each of the above standards is then obtained. A curve such as is shown in FIG. 5 is obtained. Of course there would be one such curve for each of Standards 1 through 5. These curves are then used to obtain the intensity which corresponds to the actual known concentrations of $Ag_1$ and $Ag_2$. In accordance with the present invention, this is done as follows:

Referring to the decay time curves for each of the standards, and using FIG. 5 as illustrative, the intensity at time zero for that portion of the curve which corresponds to the antigen of interest is obtained by extrapolation to the time zero intensity coordinate. That Region of the curve of the antigen of interest is determined simply by referring to the Reference Decay Time Curve (or the decay time, if desired) prepared for that antigen/antibody complex. Thus, for example, Region III of FIG. 2 is known to correspond to that obtained on the antigen of FIG. 4 because of the coincidence of their longer decay time sections of the curve (or the correspondence of the decay times, if desired) relative to other components of the mixture.

The intensity at time zero is as previously discussed obtained by extrapolating Portion III of FIG. 2 to time zero using standard curve fitting techniques. The same is done for Portion II of FIG. 2 resulting in intercepts m and n on FIG. 5.

Linear regression analysis or preferably, a least squares method optimized by a Simplex routine, is performed so as to obtain the intensity intercepts. Standard visual curve fitting techniques can also be employed to obtain the straight line intercept at time zero. In those areas where the curve is relatively linear, deviations of less than 5% are routinely obtained. That is, two or more independent curve fitting events will generally be within 5% of one another. Where the curve is generally non-linear, that is near the ends, conventional curve fitting will probably result in precision of about 10% of less. While suitable curves and results are generally obtained using visual curve fitting techniques it is preferred to use conventional computer linear regression programs or the least squares method to obtain intercepts which are subject always to the same set of instructions and not the subjective views of individual curve fitting. It is well within the skill of the art to select appropriate curve fitting models known in the art. In the preferred mode of this invention a commercially available computer program is employed.

Figure 6:
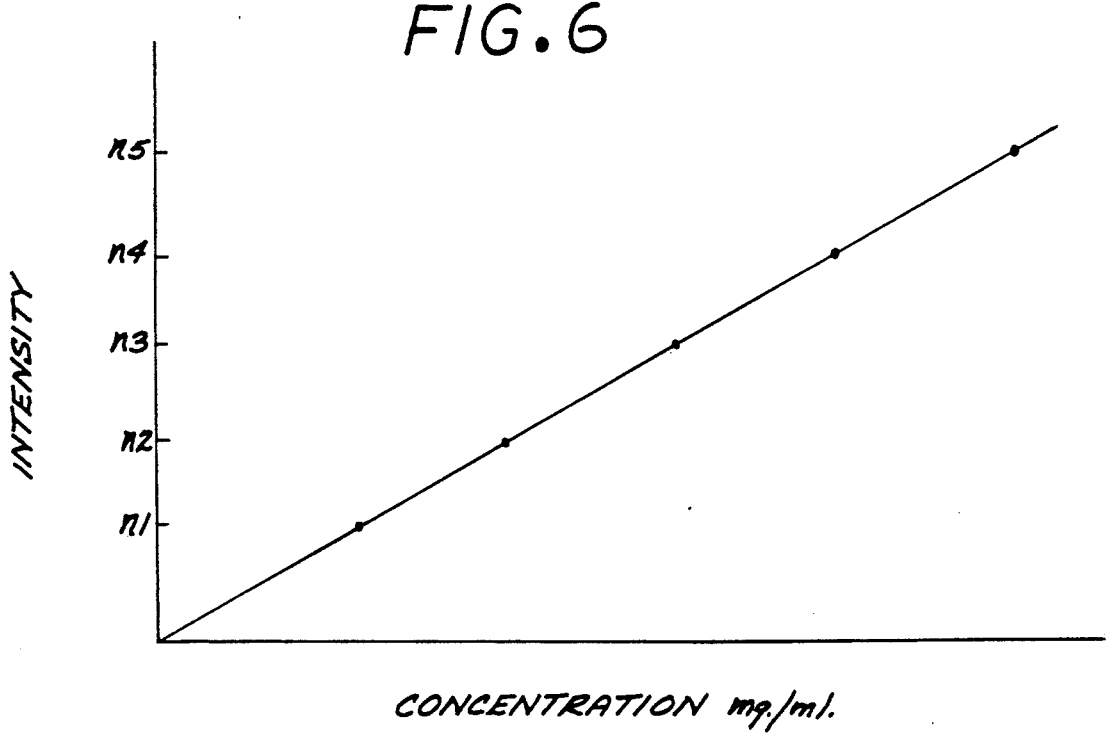
FIGS. 6 and 7 are standard curves for antigens Ag1 and Ag2.
Figure 7:
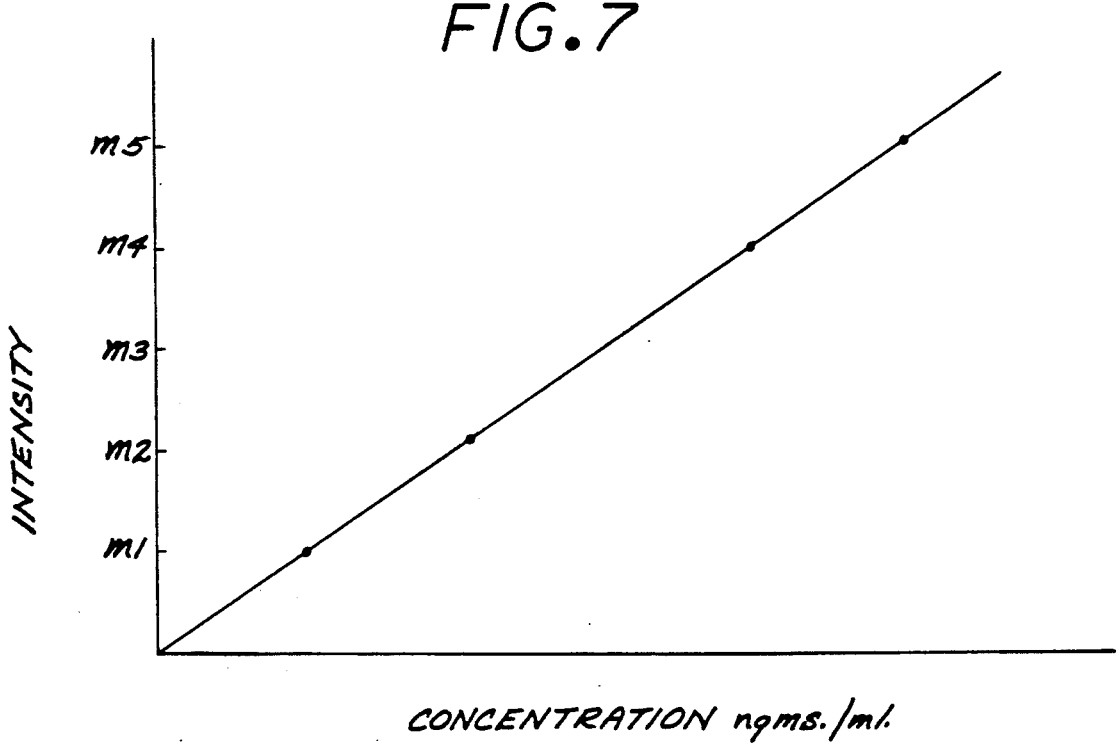

Once the zero time intercepts are obtained, actual preparation of the standard curves may be achieved. Since, according to the present invention, these time zero intensities are proportional to the concentration of the target antigen, they may be plotted against the known concentrations of $Ag_1$ and $Ag_2$ used in the standards. Separate curves are prepared for each of $Ag_1$ and $Ag_2$ as will be apparent. When this is done, curves will be obtained, typified by FIGS. 6 and 7, which correlate known concentrations with fluorescent intensity obtained in the system.

The foregoing shows the general procedure for carrying out the present invention. The following demonstrates the results obtained on two ligands of interest in a control serum, in this case antigens $T_3$ (Triiodothyronine), and IgG (Immunoglobulin). These ligands are present in widely differing concentrations in humans, $T_3$ being in the nanogram/deciliter region and IgG being in the milligram region. Those skilled in the art will also appreciate the fact that these ligands are widely different in size, IgG being a large molecule and $T_3$ being a small hapten. The determination of a large molecule in the presence of a small one and vice-versa is a very difficult task to accomplish using prior art techniques.

A series of mixed standards was prepared in phosphate buffer (also containing thimerosal and BSA) in the following concentrations:

| $T_3$ Cond. ng/dl | IgG Conc. mg/dl |
|---|---|
| 0 + | 0 |
| 50 + | 500 |
| 100 + | 1000 |
| 200 + | 2000 |

A solution containing a mixture of pyrene methyl labelled anti-$T_3$ ($10^{-7}$M) and pyrene butyl labelled anti-IgG ($10^{-7}$M) was prepared in phosphate buffer containing thimerosal and BSA. In all cases 200 ul of standard or sample was pipetted into 4 ml of the fluorescent labelled antiserum mixture. The solutions were mixed and placed at 4° C. overnight. Each solution was then analyzed for decay time fluorescence and decay time curves prepared.

Figure 8:
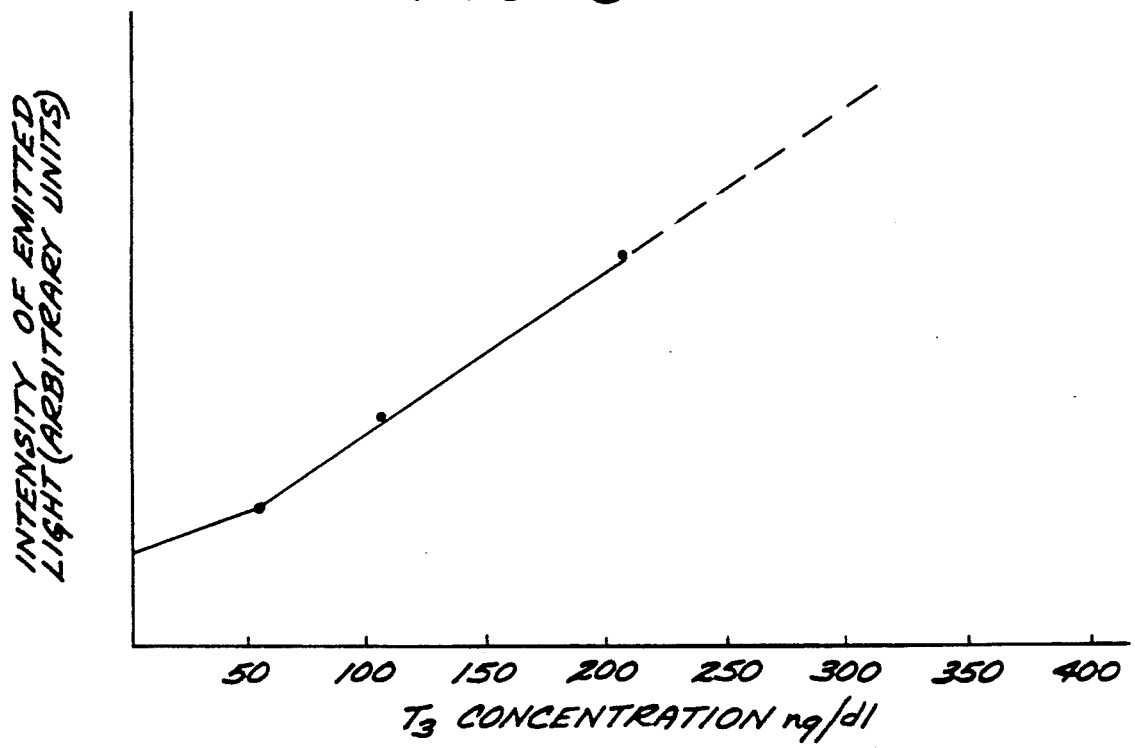
FIG. 8 is a standard curve for T3.
Figure 9:
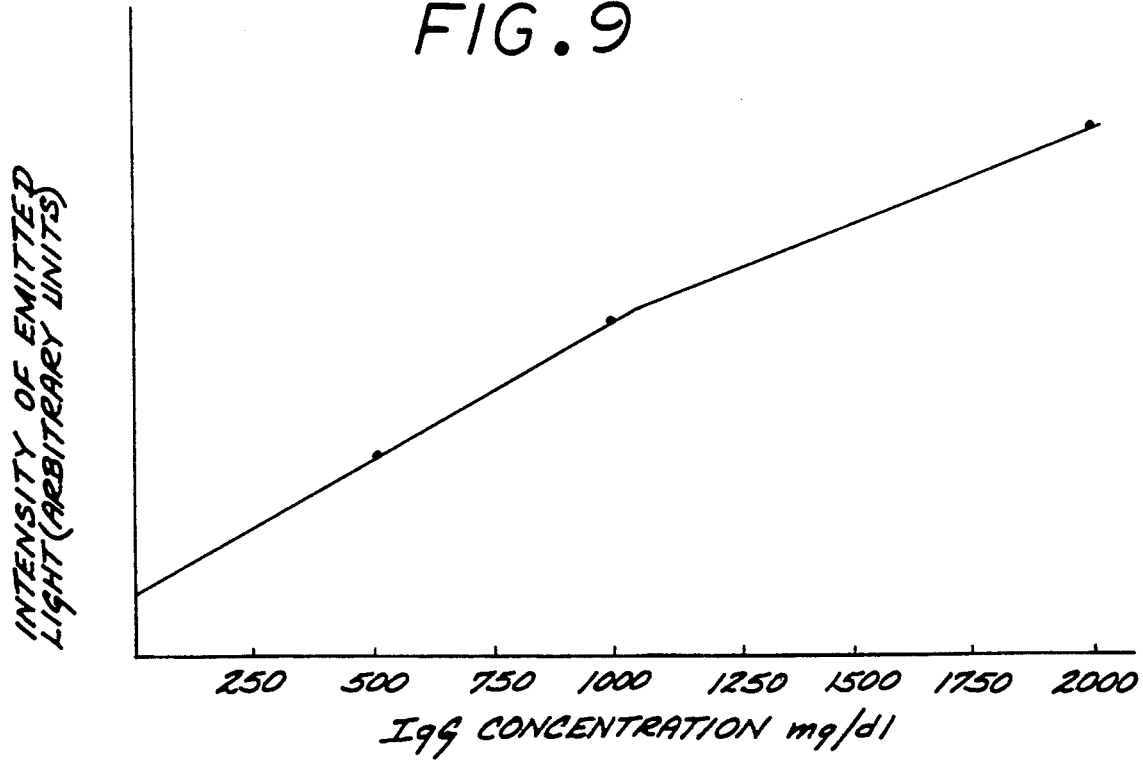
FIG. 9 is a standard curve for IgG.

The different decay times of the two labelled antisera allowed clear separation of the intensity of the $T_3$ component from the IgG contribution. The fluorescent intensity of each sample was determined both visually and by linear regression to obtain the zero time intensities. A plot of the intensity vs. the concentration of each control is shown in FIG. 8 ($T_3$) and FIG. 9 (IgG).

Two human control serum samples with values of T3 and IgG established by reference techniques were then assayed by the method of the present invention under the same conditions as the controls above. In both cases the fluorescent intensity of the IgG and T3 functions were compared to the respective standard curves and the IgG and T3 concentrations recorded.

FIG. 10 shows the decay time curve obtained on Sample 1, and FIG. 11 that was obtained in Sample 2. The intensity intercept of the pyrene butyl Anti IgG-IgG complex is 2.8. That portion of the curve attributed to that complex was known from a prior Reference Decay Time Curve which had established the complex to be in the 40-140 nanosecond decay time range (decay time 77-78 nanoseconds).

In a similar fashion the intensity of the pyrene methyl-Anti $T_3$- $T_3$ complex was determined to be 3.7, the Reference Decay Time Curve being in the 20-100 nanosecond range (decay time 40-56 nanoseconds, depending on method for determining). See FIG. 11.

The above intensities were then read off the standard curve to determine the concentration of $T_3$ and IgG, respectively, with the following results.

| | T3 ng/dl | | IgG g/dl | |
|---|---|---|---|---|
| | Established Conc. Range | Conc. by DTF | Established Conc. Range | Conc. by DTF |
| Sample 1 | 154 ± 25 | 136 | 982 ± 180 | 1150 |
| Sample 2 | 343 ± 30 | 360 | 902 ± 180 | 1069 |

Sample 1, a patient sample measured 800 and 850 in intensities in two separate runs conducted 3 days apart.

While in the foregoing ligands are reacted with binding molecules which are antibodies, the invention may as well be carried out with non-immunological binding partners such as DNA and complementary DNA probes, biological receptors, specific protein binding agents, and the like. If it were desired to detect presence only, the determination of a time zero intensity value could be dispensed with.

Similarly, the invention may also be employed when other assay formats are employed, such as competitive binding. In such a case, the fluorescent label is usually attached to a ligand corresponding to the target ligand and the two made to compete for reaction with a known amount of its binding molecule.

The primary components of a decay time fluorometer (DTF) used in the present invention are typically as follows: 1. Light pulser, typically a nitrogen pulsed laser which generates a short, preferably less than 3 nanosecond wide pulse of light that stimulates the test sample in the fluorometer to emit light at its fluorescent frequencies. This light pulser may include a nitrogen flashlamp or any nitrogen laser, a sufficient short pulse width such as a pumped dye laser or a nitrogen flashlamp. For high sensitivity performance, a laser light source is most preferred. The light emission of the test sample is detected by a photomultiplier tube (PMT) of high light sensitivity preferably with at least nine stages. The output of the PMT is then sent to a decay time computer for measurement of the time interval between the starting peak amplitude of the pulse and various amplitude levels on the time decay curve. This series of amplitude levels generates the fluorescent decay time—amplitude function. Typically, one hundred or more "stop" levels may be used to define a high resolution time decay function.

The time decay function (log vs. linear) is then in a preferred embodiment transmitted to a decomposition microcomputer which performs the analysis necessary to determine the individual decay functions that comprise the composite decay time function. The results of the analysis, which include the concentration and decay time of each of the light emitting elements of the test mixture, is then tabulated on a printer.

The function of the decay time computer is to measure the decay time function to an accuracy of preferably 0.1 nanoseconds. This measurement determines the time interval between the amplitude-time points that make up the decay time functions. Measurement to an accuracy of 0.1 nanosecond with current electronic technology is possible with state of the art circuit arrangements that overcome the basic count resolution of high speed ECL circuits (around 5 nanoseconds).

The final major component in the system, the decomposition microcomputer and its associated printer, is of conventional design. A Texas Instrument 9900 microprocessor is suitable as the primary processing element in the microcomputer. The microprocessor is programmed to provide for the decomposition of the composite time decay function into its constituent time decay elements. This decomposition takes place in the presence of noise generated in the measurement process. The decomposition algorithm used enables the determination of accurate decay time and concentration values even in the presence of significant noise levels.

The fluorophores which may be used in the present invention are those which typically can exhibit a decay time curve in the zero to 150 nanosecond range especially when attached to a ligand or its binding molecule or act as part of an ligand/binding molecule complex. Members of the class of pyrenes such as pyrene carboxylic acids, pyrene alkyls, halogenated pyrene alkyls and coronenes are especially suitable. Dansyls may also be used. (See cpd #11 below). These materials absorb excited light at 340 nanometer wavelengths and emit fluorescence beyond 380 nanometers. Most preferred are pyrene methyl and pyrene butyl for use in the present invention. The following represents an illustrative sampling of suitable fluorophor radicals, the open bond being attached to the ligand or its binding molecule:

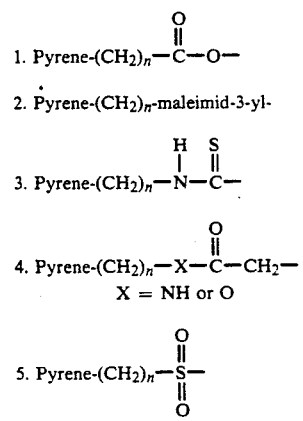

Wherein n = 0 to 21

In each of the above cases one of the H's in the $CH_2$-radical may be a halogen (e.g. Cl, Fl, Br)

| | | |
|---|---|---|
| 6. | 1-Pyrene Butyryl- | this is the pyrene butyl referred to in the present invention. This is compound 1 above with n = 3. Butyryl in the above may be substituted by Valeroyl or Propionyl |
| 7. | 1-(pyrene succin-3-yl)- | |
| 8. | 1-Pyrenesufonyl- (compound 5 above with n = 0) | |
| 9. | 1-Pyrenethioureidyl | |
| 10. | 1-(Pyrenemethoxy(carbonyl(methyl))- | This compound #4 with n = 1 and X = 0 and is designated as pyrene methyl herein. |
| 11. | 2-Dialkyaminoaphthalene-5-sulfonyl- | |

While the foregoing invention has been described with particular reference to specific embodiments, components and materials, it will be appreciated that various modifications can be made without deviating from the scope of the present invention. For example, the labelled immunological material, while described as being the labelled antibody could as well be a labelled antigen when an antibody is sought as the target compound.

What is claimed is:

1. A homogeneous, fluorescent specific binding method for detecting the presence and concentration of at least two target ligands in a sample containing interfering fluorescing species which comprises:

a. treating a sample containing at least two target ligands with at least two specific binding molecules, each reactive with a different one of said target ligands and provided with a different fluorescent label, to form thereby in said sample, at least two ligand fluorescently labelled specifically binding molecule complexes, wherein the fluorescent decay time of one of the complexes is demonstrably shorter than that of the other,
b. exciting the sample with a source of exciting light to induce fluorescence in each of the complexes and interfering fluorescing species in said sample,
c. measuring the decay of the fluorescence so induced and determining its relationship to time,
d. determining from said relationship, values for a decay time-fluorescence intensity curve for said sample,
e. locating from among said values regions of values which correspond to the fluorescent contributions of each of the complexes,
f. determining for each of said regions, a first fluorescence intensity value at time zero, and
g. comparing the first intensity value at time zero for each of said complexes with a second fluorescent intensity value at time zero obtained on a known concentration of each of said complexes to thereby obtain the concentration of each of the target ligands.

2. The method of claim 1 wherein the exciting light is obtained from a pulsed laser.

3. The method of claim 2 wherein the laser is a nitrogen laser.

4. The method of claim 3 wherein the exciting light is at a wavelength of about 340 nanometers.

5. The method according to claim 1 wherein each of the fluorescent labels is a fluorescing pyrene derivative.

6. The method according to claim 5 wherein at least one of the pyrenes is pyrene methyl.

7. The method according to claim 5 wherein at least one of the pyrenes is pyrene butyl.

8. The method according to claim 1, wherein two fluorescently labelled binding molecules are employed.

9. The method according to claim 8 wherein one fluorescent label is pyrene methyl and is used on the specific binding molecule of the complex expected to have a shorter decay time and the other is pyrene butyl and is used on the specific binding molecule of the complex expected to have a longer decay time.

10. The method of claim 1, wherein each ligand is an antigen and each binding molecule is an antibody reactive therewith.

11. The method according to claim 10 wherein one antigen is a large molecule and another is a small molecule.

12. The method of claim 1 wherein the sample is a body fluid.

13. The method of claim 12 wherein the body fluid is serum.

14. The method of claim 12 wherein the body fluid is urine.

15. The method according to claim 1, wherein step f. is achieved by extrapolating said values to intensity time zero by linear regression analyses.

* * * * *